(12) United States Patent
Adam et al.

(10) Patent No.: US 8,497,377 B2
(45) Date of Patent: Jul. 30, 2013

(54) PROCESS FOR PREPARING PRADOFLOXACIN

(75) Inventors: Thomas Adam, Wuppertal (DE); Ralf Wischnat, Bergisch Gladbach (DE); Klaus Weidemann, Wuppertal (DE)

(73) Assignee: Bayer Intellectual Property GmbH (DE)

( * ) Notice: Subject to any disclaimer, the term of this patent is extended or adjusted under 35 U.S.C. 154(b) by 360 days.

(21) Appl. No.: 12/442,680

(22) PCT Filed: Oct. 7, 2007

(86) PCT No.: PCT/EP2007/008687
§ 371 (c)(1),
(2), (4) Date: Mar. 24, 2009

(87) PCT Pub. No.: WO2008/046532
PCT Pub. Date: Apr. 24, 2008

(65) Prior Publication Data
US 2009/0318700 A1      Dec. 24, 2009

(30) Foreign Application Priority Data
Oct. 20, 2006   (DE) .................. 10 2006 049 520

(51) Int. Cl.
*C07D 471/02*   (2006.01)

(52) U.S. Cl.
USPC ........................................ 546/113

(58) Field of Classification Search
USPC ........................................ 546/113
See application file for complete search history.

(56) References Cited

U.S. PATENT DOCUMENTS

| | | | |
|---|---|---|---|
| 6,229,040 B1 | 5/2001 | Marhold et al. | |
| 6,278,013 B1 | 8/2001 | Bartel et al. | |
| 6,462,218 B1 | 10/2002 | Hallenbach et al. | |
| 6,649,762 B1 | 11/2003 | Rast et al. | |
| 6,664,268 B1 * | 12/2003 | Himmler et al. | 514/300 |
| 2004/0247560 A1 | 12/2004 | Dirk et al. | |
| 2006/0034926 A1 | 2/2006 | Fraatz et al. | |
| 2006/0177414 A1 | 8/2006 | Mertin et al. | |
| 2007/0082911 A1 | 4/2007 | Daube et al. | |
| 2007/0196466 A1 | 8/2007 | Bosche et al. | |
| 2009/0011045 A1 | 1/2009 | Mertin et al. | |

FOREIGN PATENT DOCUMENTS
DE      19908449      *   8/2000

OTHER PUBLICATIONS
PCT International Search Report dated Feb. 26, 2008, 4 pgs.

* cited by examiner

*Primary Examiner* — Nizal Chandrakumar

(57) ABSTRACT

The invention relates to an improved process for preparing pradofloxacin, in which the substituent in the 7 position is introduced by nucleophilic substitution in an N-methylpyrrolidone-ethanol solvent mixture.

2 Claims, No Drawings

PROCESS FOR PREPARING PRADOFLOXACIN

The invention relates to an improved process for preparing pradofloxacin, in which the substituent in the 7 position is introduced by nucleophilic substitution in an N-methylpyrrolidone-ethanol solvent mixture.

The quinolone antibiotic pradofloxacin of the formula (I)

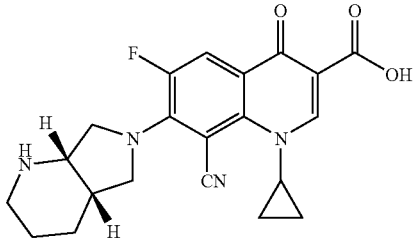

(I)

and its preparation have already been described in WO 97/31001. Particular precursors, intermediates and early process steps are disclosed in WO98/47862 and WO99/06360.

The key step in the preparation is the reaction of the corresponding 7-halocyanofluoroquinolonecarboxylic acid, especially of the 7-chloro-8-cyano-1-cyclopropyl-6-fluoro-1,4-dihydro-4-oxo-3-quinolinecarboxylic acid of the formula (II)

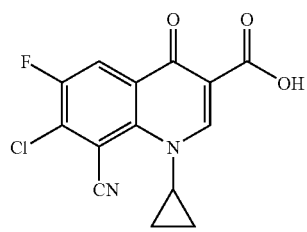

(II)

with (1S,6S)-2,8-diazabicyclo[4.3.0]nonane of the formula (III) (also known as S,S-pyrrolopiperidine)

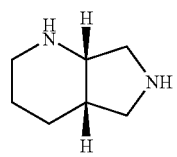

(III)

in a nucleophilic substitution reaction. It is known that such nucleophilic substitutions are preferably performed in polar aprotic solvents. For instance, WO 97/31001 proposes, in general form, solvents including dimethyl sulphoxide, N,N-dimethylformamide, N-methylpyrrolidone, hexamethylphosphoramide, sulfolane and acetonitrile for corresponding reactions; alcohols, for example methanol, ethanol, n-propanol, isopropanol and others, are likewise proposed there as solvents for these purposes.

It has been found that, surprisingly, a particularly suitable solvent for this reaction is a mixture of N-methylpyrrolidone with ethanol.

The invention relates to a process for preparing pradofloxacin of the formula (I)

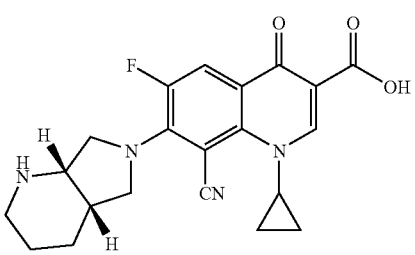

(I)

by reacting, optionally in the presence of a base, the 7-chloro-8-cyano-1-cyclopropyl-6-fluoro-1,4-dihydro-4-oxo-3-quinolinecarboxylic acid of the formula (II)

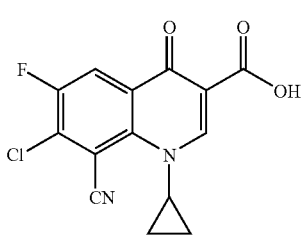

(II)

with (1S,6S)-2,8-diazabicyclo-[4.3.0]nonane of the formula (III)

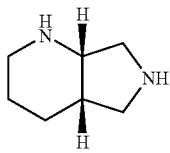

(III)

in a solvent mixture of N-methylpyrrolidone and ethanol.

Typically, the solvent mixture contains at least 20% by weight of ethanol. Particular preference is given to a mixture with at least 50% by weight of ethanol. The mixture preferably contains not more than 95% by weight of ethanol. Particular preference is given to mixtures with 70 to 90% by weight of ethanol.

For the ratio of (1S,6S)-2,8-diazabicyclo[4.3.0]nonane to 7-chloro-8-cyano-1-cyclopropyl-6-fluoro-1,4-dihydro-4-oxo-3-quinolinecarboxylic acid, WO 97/31001 specifies a wide range which ranges from equimolar amounts up to a large excess of (1S,6S)-2,8-diazabicyclo[4.3.0]nonane. In the development of a synthesis performable on the industrial scale, the person skilled in the art will routinely select an excess of (1S,6S)-2,8-diazabicyclo[4.3.0]nonane: (1S,6S)-2,8-diazabicyclo[4.3.0]nonane has two basic ring nitrogen atoms which can both react nucleophilically with the 7-chloro-8-cyano-1-cyclopropyl-6-fluoro-1,4-dihydro-4-oxo-3-quinolinecarboxylic acid. In the case of too low an amount of (1S,6S)-2,8-diazabicyclo[4.3.0]nonane, the person skilled in the art would thus expect the formation of undesired by-products by linkage of the second ring nitrogen atom of the (1S,6S)-2,8-diazabicyclo[4.3.0]nonane with a further molecule of 7-chloro-8-cyano-1-cyclopropyl-6-fluoro-1,4-dihydro-4-oxo-3-quinolinecarboxylic acid.

Unexpectedly, it has been found to be particularly favourable to use the (1S,6S)-2,8-diazabicyclo[4.3.0]nonane, in relation to the 7-chloro-8-cyano-1-cyclopropyl-6-fluoro-1,4-dihydro-4-oxo-3-quinolinecarboxylic acid, only in a small molar excess, typically 1.01 to 1.30 times, preferably 1.05 to 1.25 times, the molar amount based on the amount of 7-chloro-8-cyano-1-cyclopropyl-6-fluoro-1,4-dihydro-4-oxo-3-quinolinecarboxylic acid.

The reaction of (1S,6S)-2,8-diazabicyclo[4.3.0]nonane with 7-chloro-8-cyano-1-cyclopropyl-6-fluoro-1,4-dihydro-4-oxo-3-quinolinecarboxylic acid is effected in the presence of a base which binds the acid formed. Such a base may, for example, be an excess of (1S,6S)-2,8-diazabicyclo[4.3.0]nonane, which is less preferred for the abovementioned reasons. It is possible in general to use inorganic and organic bases. These include, for example, the alkali metal hydroxides, alkali metal carbonates, organic amines and amidines. Preference is given to organic bases, especially tertiary amines. Specific particularly suitable examples include: 1,4-diazabicyclo[2.2.2]octane (DABCO), 1,8-diazabicyclo[5.4.0]undec-7-ene (DBU), triethylamine, tributylamine and especially diisopropylethylamine.

The reaction can be performed in a wide temperature range of 0 to 200° C., preferably 20 to 180° C. The reaction is effected typically at standard pressure, but performance at elevated pressure, for example at 1 to 100 bar, preferably 1 to 10 bar, is conceivable.

Under the inventive conditions, the reaction can be performed reproducibly with good yield, the pradofloxacin is obtained in very good purity, the complexity of the purification of the end product can be reduced significantly, further purification steps are generally not required. Especially in the preparation on the industrial scale, these advantages are of great significance.

Pradofloxacin is a highly effective novel quinolone antibiotic; its antibacterial action and indications, use forms and suitable formulations have already been disclosed in the prior art; see, for example, WO 97/31001, WO 03/007995, WO 03/101422, WO 04/082658, WO 05/018641, WO 05/044271 and WO 06/061156.

EXAMPLE 100 g of 7-chloro-8-cyano-1-cyclopropyl-6-fluoro-1,4-dihydro-4-oxo-3-quinolinecarboxylic acid are reacted with 48 g of (1S,6S)-2,8-diazabicyclo[4.3.0]nonane at elevated temperature (>70° C.) in a mixture of ethanol and N-methylpyrrolidone (80/20 w/w) with addition of an excess of diisopropylethylamine. After cooling, a yield of 90% of theory is obtained.

The invention claimed is:
1. Process for preparing pradofloxacin of the formula (I)

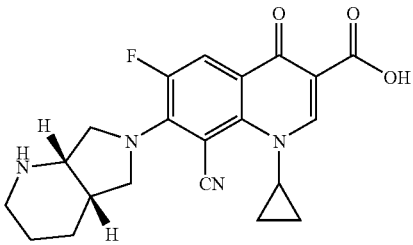

by reacting, optionally in the presence of a base, the compound of the formula (II)

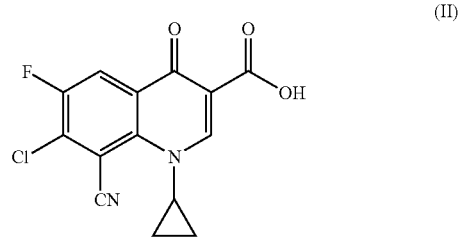 [SMILES: N#Cc1c(Cl)c(F)cc2c(=O)c(C(=O)O)cn(C3CC3)c12]

with (1S,6S)-2,8-diazabicyclo-[4.3.0]nonane of the formula (III)

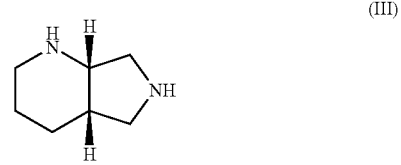

in a solvent mixture of N-methylpyrrolidone and ethanol, wherein the solvent mixture contains 70 to 90% by weight of ethanol and 30 to 10% by weight N-methylpyrrolidone, wherein the reaction is performed at a temperature range of from 20 to 180° C.

2. Process according to claim 1, wherein the (1S,6S)-2,8-diaza-bicyclo[4.3.0]nonane of the formula (III) is used in a molar ratio to the 7 chloro-8-cyano-1-cyclopropyl-6-fluoro-1,4-dihydro-4-oxo-3-quinolinecarboxylic acid of the formula (II) of 1:1.01 to 1:1.30.

* * * * *